(12) United States Patent
Taninai et al.

(10) Patent No.: US 10,881,366 B2
(45) Date of Patent: Jan. 5, 2021

(54) RADIOGRAPHIC IMAGE DETECTION DEVICE

(71) Applicant: FUJIFILM Corporation, Tokyo (JP)

(72) Inventors: Koji Taninai, Ashigarakami-gun (JP); Masateru Tateishi, Ashigarakami-gun (JP); Sho Shimizukawa, Ashigarakami-gun (JP); Hiroki Koketsu, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 63 days.

(21) Appl. No.: 16/292,699

(22) Filed: Mar. 5, 2019

(65) Prior Publication Data

US 2019/0274648 A1 Sep. 12, 2019

(30) Foreign Application Priority Data

Mar. 6, 2018 (JP) .................. 2018-039375

(51) Int. Cl.
*A61B 6/00* (2006.01)
*G01T 1/20* (2006.01)
*G01T 1/161* (2006.01)
*G01T 7/00* (2006.01)

(52) U.S. Cl.
CPC .......... *A61B 6/4283* (2013.01); *A61B 6/4208* (2013.01); *A61B 6/4233* (2013.01); *A61B 6/505* (2013.01); *G01T 1/161* (2013.01); *G01T 1/20* (2013.01); *G01T 7/00* (2013.01); *G01T 1/2018* (2013.01)

(58) Field of Classification Search
CPC ... A61B 6/4208; A61B 6/4233; A61B 6/4283; A61B 6/505; G01T 1/161; G01T 1/20; G01T 1/218; G01T 7/00; G01T 1/2018
See application file for complete search history.

(56) References Cited

U.S. PATENT DOCUMENTS

| 2014/0226795 A1* | 8/2014 | Kitano | A61B 6/4283 378/189 |
| 2014/0270092 A1* | 9/2014 | Ogura | G03B 42/04 378/189 |
| 2015/0182182 A1* | 7/2015 | Tajima | A61B 6/542 378/189 |
| 2015/0189194 A1* | 7/2015 | Tajima | A61B 6/488 378/62 |
| 2015/0342553 A1* | 12/2015 | Sato | G01T 7/00 250/336.1 |
| 2015/0363926 A1* | 12/2015 | Enomoto | A61B 6/542 382/132 |

(Continued)

FOREIGN PATENT DOCUMENTS

JP 2013-250103 A 12/2013

*Primary Examiner* — Mark R Gaworecki
(74) *Attorney, Agent, or Firm* — Birch, Stewart, Kolasch & Birch, LLP

(57) ABSTRACT

A first sensor panel, a second sensor panel, a first circuit unit, and a second circuit unit are accommodated in a conductive housing of an electronic cassette. Of circuit substrates included in the first and second circuit units, a control substrate having a control circuit for controlling the operation of each of the first and second sensor panels is fixed to an inner surface of the housing through a metal spacer. The first and second sensor panels are attached to a front surface of a base. The base is fixed to the inner surface of the housing through a resin adhesive.

10 Claims, 6 Drawing Sheets

(56) References Cited

U.S. PATENT DOCUMENTS

| | | | |
|---|---|---|---|
| 2016/0081638 A1* | 3/2016 | Ogura | A61B 6/4291 378/185 |
| 2016/0081649 A1* | 3/2016 | Enomoto | A61B 6/56 378/189 |
| 2018/0011206 A1* | 1/2018 | Ichimura | G01T 7/00 |
| 2018/0234642 A1* | 8/2018 | Langley | H04N 5/232 |

* cited by examiner

RADIOGRAPHIC IMAGE DETECTION DEVICE

CROSS-REFERENCE TO RELATED APPLICATIONS

This application claims priority under 35 U.S.C § 119(a) to Japanese Patent Application No. 2018-039375 filed on 6 Mar. 2018. The above application is hereby expressly incorporated by reference, in its entirety, into the present application.

BACKGROUND OF THE INVENTION

1. Field of the Invention

The present invention relates to a radiographic image detection device.

2. Description of the Related Art

In a medical field, a diagnosis is made on the basis of a radiographic image detected by a radiographic image detection device. The radiographic image detection device comprises a sensor panel, a circuit unit, and a housing. In the sensor panel, a plurality of pixels that accumulate charge in response to radiation which has been emitted from a radiation source and then transmitted through a subject (patient) are two-dimensionally arranged. The radiographic image detection device comprising the sensor panel is also called a flat panel detector (FPD). The circuit unit converts the charge accumulated in the pixels of the sensor panel into a digital signal and outputs the digital signal as a radiographic image. The circuit unit includes a circuit substrate on which various circuits are mounted. The housing is, for example, a box having a rectangular parallelepiped shape and accommodates a sensor panel and a circuit unit. The housing is made of a conductive material, such as a resin mixed with carbon fibers, a resin mixed with an aluminum or nickel filler, an aluminum alloy, or a magnesium alloy.

A radiographic image detection device disclosed in JP2013-250103A comprises a base having a thin plate shape. A sensor panel is attached to a front surface of the base and all of a plurality of circuit substrates are mounted and fixed to a rear surface of the base. A structure for connecting a ground wire of the circuit substrate to a housing is disclosed in paragraph [0074] of JP2013-250103A. In JP2013-250103A, since the ground wire of the circuit substrate is connected to the housing, electromagnetic noise generated by the circuit substrate is unlikely to be propagated to the sensor panel and the effect of preventing the degradation of the quality of a radiographic image caused by the electromagnetic noise generated by the circuit substrate is obtained.

SUMMARY OF THE INVENTION

However, in JP2013-250103A, all of the circuit substrates are mounted and fixed to the rear surface of the thin-plate-shape base having the front surface to which the sensor panel is attached. Therefore, it is highly likely that electromagnetic noise generated by the circuit substrate is propagated from the base to the sensor panel through a fixing portion for fixing the circuit substrate to the base and the quality of a radiographic image is degraded.

An object of the invention is to provide a radiographic image detection device that can reduce the possibility that electromagnetic noise generated by a circuit substrate will be propagated to a sensor panel and the quality of a radiographic image will be degraded.

In order to solve the above-mentioned problems, according to the invention, there is provided a radiographic image detection device comprising: a sensor panel in which pixels that accumulate charge in response to radiation, which has been emitted from a radiation source and transmitted through a subject, are two-dimensionally arranged; a circuit unit that converts the charge into a digital signal, outputs the digital signal as a radiographic image, and includes circuit substrates on which various circuits are mounted; a conductive housing that accommodates the sensor panel and the circuit unit; and a conductive substrate fixing portion that fixes a specific substrate which is at least one of the circuit substrates to the housing. The specific substrate is fixed to the housing through the substrate fixing portion.

Preferably, the radiographic image detection device further comprises a panel fixing portion that fixes the sensor panel to the housing. Preferably, the panel fixing portion has a higher impedance than the substrate fixing portion.

Preferably, the radiographic image detection device further comprises a base having a front surface to which the sensor panel is attached. Preferably, the panel fixing portion fixes the base to the housing and the sensor panel is indirectly fixed to the housing through the base.

Preferably, the substrate fixing portion is a spacer that is made of metal, is vertically provided on an inner surface of the housing, and is fastened and fixed to the specific substrate and the panel fixing portion is an adhesive that is made of a resin and bonds an outer surface of the base and the inner surface of the housing. The circuit substrates other than the specific substrate are mounted and fixed to a rear surface of the base.

Preferably, the panel fixing portion directly fixes the sensor panel to the housing.

Preferably, the substrate fixing portion is a spacer that is made of metal, is vertically provided on an inner surface of the housing, and is fastened and fixed to the specific substrate and the panel fixing portion is an adhesive that is made of a resin and bonds an outer surface of the sensor panel and the inner surface of the housing.

Preferably, the specific substrate fixed to the housing through the substrate fixing portion includes a control substrate having a control circuit that controls an operation of the sensor panel.

Preferably, two sensor panels are provided and are sequentially arranged in a thickness direction and two circuit units are provided for the two sensor panels, respectively. In this case, preferably, two radiographic images output from the two circuit units are used to calculate an index value related to bones.

According to the invention, a specific substrate which is at least one of the circuit substrates is fixed to the housing through a conductive substrate fixing portion. Therefore, it is possible to provide a radiographic image detection device which can reduce the possibility that electromagnetic noise generated by a circuit substrate will be propagated to a sensor panel and the quality of a radiographic image will be degraded.

DESCRIPTION OF THE PREFERRED EMBODIMENTS

First Embodiment

Figure 1:
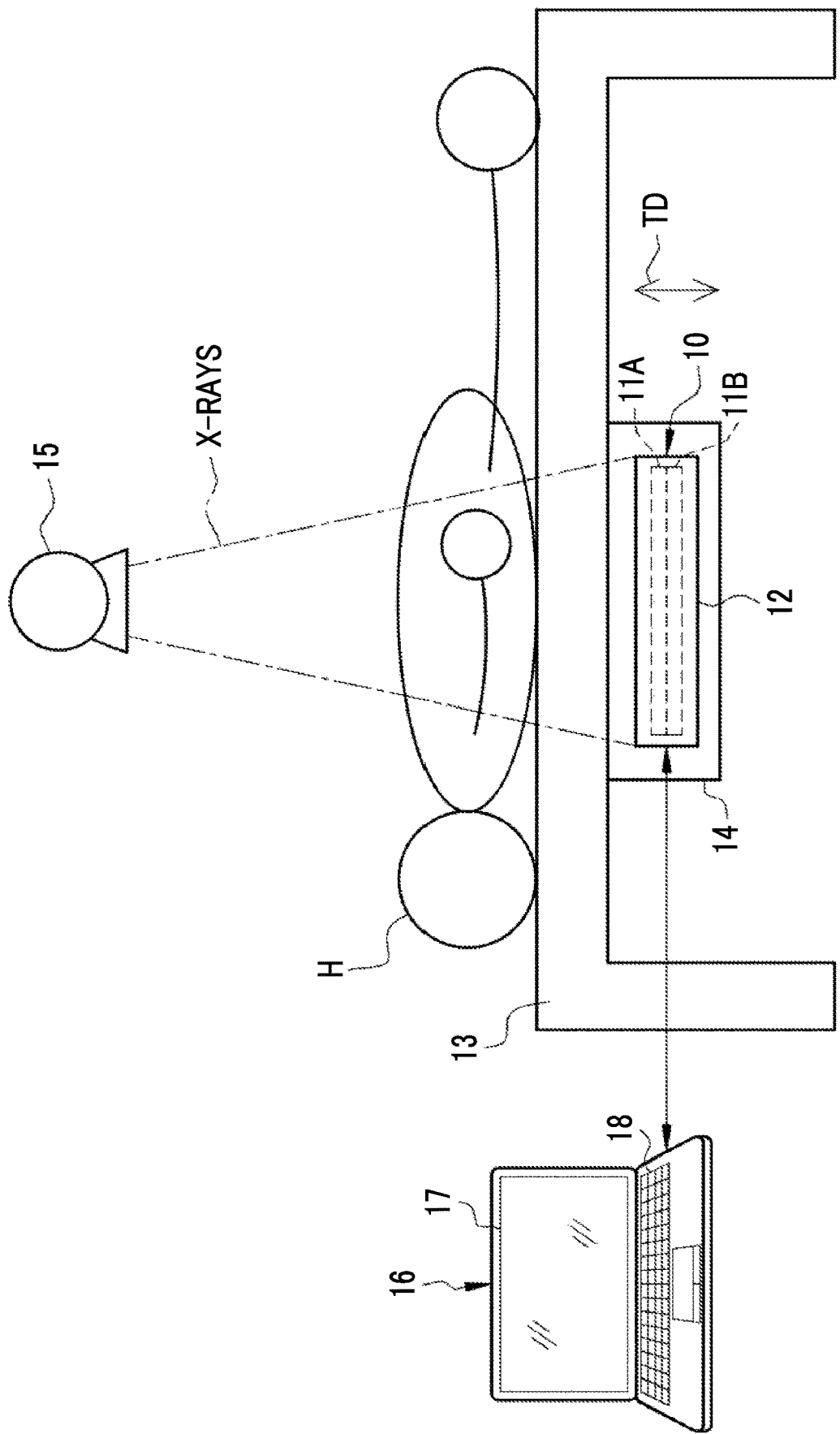
FIG. 1 is a diagram illustrating an aspect of X-ray imaging.

In FIG. 1, an electronic cassette 10 corresponding to a radiographic image detection device according to the invention has a first sensor panel 11A and a second sensor panel 11B which are accommodated in a housing 12. The first and second sensor panels 11A and 11B are thin plates having a rectangular shape in a plan view and are sequentially arranged in a thickness direction TD.

The housing 12 is a portable box having a rectangular parallelepiped shape and has a size which is based on the International Organization for Standardization (ISO) 4090:2001 and is substantially equal to the size of, for example, a film cassette, an imaging plate (IP) cassette, or a computed radiography (CR) cassette. The housing 12 is made of a conductive material, such as a resin mixed with carbon fibers, a resin mixed with an aluminum or nickel filler, an aluminum alloy, or a magnesium alloy.

The electronic cassette 10 is set in a holder 14 of an imaging table 13 on which a subject H lies supine. Then, the electronic cassette 10 receives X-rays (represented by a one-dot chain line) corresponding to radiation which has been emitted from an X-ray source 15 corresponding to a radiation source and then transmitted through the subject H and detects an X-ray image corresponding to a radiographic image.

The electronic cassette 10 is connected to a console 16 and communicates with the console 16 to transmit and receive various kinds of information. Various kinds of information include, for example, the X-ray images detected by the electronic cassette 10 and an imaging menu input by an operator through the console 16. The imaging menu is, for example, a set of an imaging part, such as the head or the chest, a posture, such as an upright position, a lying position, or a sitting position, and the orientation of the subject H with respect to X-rays, such as the front, the side, or the back.

For example, the console 16 is configured by installing a control program, such as an operating system, and various application programs in a computer such as a notebook personal computer. The console 16 includes a display 17 and an input device 18 such as a touch pad or a keyboard. For example, the X-ray image transmitted from the electronic cassette 10 is displayed on the display 17.

Figure 2:
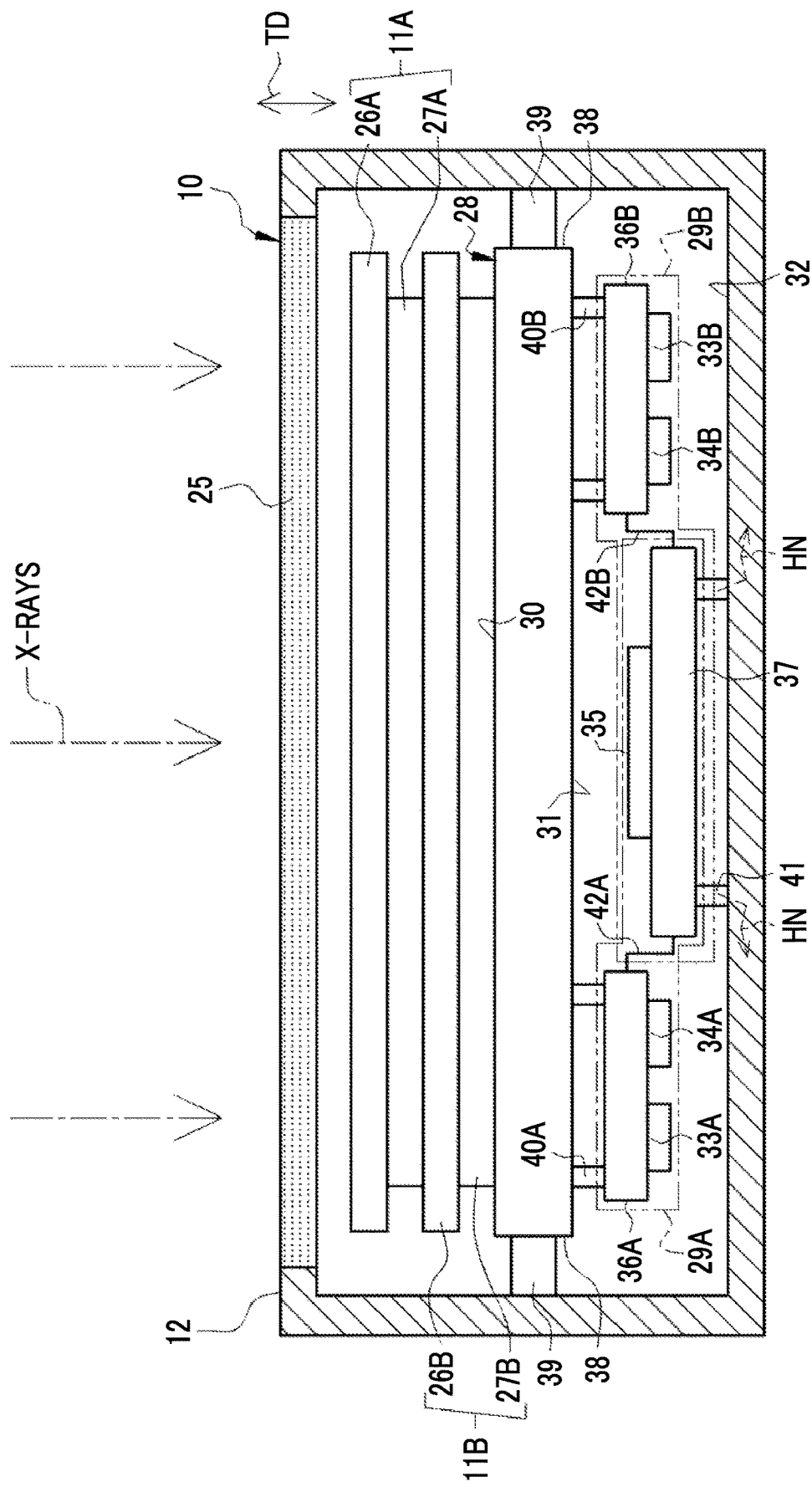
FIG. 2 is a diagram illustrating the internal structure of an electronic cassette.

In FIG. 2, a rectangular opening is formed in a front surface of the housing 12 on which X-rays are incident and a transmission plate 25 that transmits X-rays is attached to the opening. The first sensor panel 11A and the second sensor panel 11B are provided immediately below the transmission plate 25. Here, the thickness direction TD in which the first and second sensor panels 11A and 11B are sequentially arranged is a direction that is parallel to a line normal to the front surface of the housing 12 and a rear surface of the housing 12 opposite to the front surface. The first sensor panel 11A includes a first light detection substrate 26A and a first scintillator 27A. The first light detection substrate 26A and the first scintillator 27A are arranged in the order of the first light detection substrate 26A and the first scintillator 27A as viewed from the front surface of the housing 12 on which X-rays are incident. Similarly, the second sensor panel 11B includes a second light detection substrate 26B and a second scintillator 27B which are arranged in the order of the second light detection substrate 26B and the second scintillator 27B as viewed from the front surface of the housing 12. In addition, a sensor panel in which a scintillator 27 and a light detection substrate 26 are sequentially arranged as viewed from the front surface of the housing 12 may be used. Further, a direct-conversion-type sensor panel that directly converts X-rays into charge with a photoconductive film made of, for example, amorphous selenium may be used.

The first scintillator 27A has a phosphor, such as CsI:Tl (thallium-activated cesium iodide), and the second scintillator 27B has a phosphor, such as GOS ($Gd_2O_2S$:Tb, terbium-activated gadolinium oxysulfide). Each of the first and second scintillators 27A and 27B converts incident X-rays into visible light and emits the visible light. The first and second light detection substrates 26A and 26B detect the visible light emitted from the first and second scintillators 27A and 27B and convert the visible light into charge.

The housing 12 accommodates a base 28, a first circuit unit 29A, and a second circuit unit 29B in addition to the first and second sensor panels 11A and 11B. The first circuit unit 29A is for the first sensor panel 11A. The second circuit unit 29B is for the second sensor panel 11B. That is, the first circuit unit 29A and the second circuit unit 29B are provided for the first sensor panel 11A and the second sensor panel 11B, respectively.

The first and second sensor panels 11A and 11B are attached to a front surface (a surface on which X-rays are incident) 30 of the base 28. In contrast, a space for arranging circuit substrates 36A, 36B, and 37 of various circuits 33A, 33B, 34A, 34B, and 35 included in the first and second circuit units 29A and 29B is formed between a rear surface (a surface opposite to the front surface 30) 31 of the base 28 and an inner surface (an inner rear surface of the housing 12) 32 of the housing 12 which faces the rear surface 31.

A portion or all of a side surface 38 of the base 28 which is an outer surface is fixed to the inner surface (an inner side surface of the housing 12) 32 of the housing 12 by an adhesive 39 made of a resin such as an epoxy resin. The first and second sensor panels 11A and 11B are attached to the front surface 30 of the base 28. As a result, each of the first and second sensor panels 11A and 11B is indirectly fixed to the housing 12 through the base 28 and the adhesive 39. That is, the adhesive 39 corresponds to a panel fixing portion. The housing 12 accommodates a cable connector (not illustrated) that performs wired communication with the console 16 and receives power from a commercial power supply in addition to these components. The housing 12 may accommodate an antenna for wireless communication with the console 16 and a battery for wirelessly driving the electronic cassette 10.

The first circuit unit 29A includes a first gate driving circuit 33A, a first signal processing circuit 34A, and a control circuit 35. The second circuit unit 29B includes a second gate driving circuit 33B, a second signal processing circuit 34B, and the control circuit 35. That is, the control circuit 35 is shared by the first and second circuit units 29A and 29B (see FIG. 3).

The first gate driving circuit 33A and the first signal processing circuit 34A are mounted on the first circuit substrate 36A. The second gate driving circuit 33B and the second signal processing circuit 34B are mounted on the second circuit substrate 36B. The first and second circuit substrates 36A and 36B are mounted and fixed to the rear surface 31 of the base 28 through first spacers 40A and second spacers 40B which are made of metal, such as aluminum, copper, or stainless steel, respectively. The first and second spacers 40A and 40B are vertically provided on the rear surface 31 of the base 28 and are fastened and fixed to the first and second circuit substrates 36A and 36B, respectively.

The control circuit 35 is mounted on the control substrate 37. The control substrate 37 is mounted and fixed to the inner surface (the inner rear surface of the housing 12) 32 of the housing 12 through spacers 41 which are made of metal such as aluminum, copper, or stainless steel. The spacer 41 is vertically provided on the inner surface (the inner rear surface of the housing 12) 32 of the housing 12 and is fastened and fixed to the control substrate 37. The control substrate 37 is fixed to the housing 12 through the spacers 41. That is, the spacer 41 corresponds to a substrate fixing portion. The control substrate 37 corresponds to a specific substrate. The first and second circuit substrates 36A and 36B correspond to circuit substrates other than the specific substrate.

The first and second circuit substrates 36A and 36B and the control substrate 37 are electrically connected to each other by a first flexible circuit substrate 42A and a second flexible circuit substrate 42B. The first and second light detection substrates 26A and 26B and the first and second circuit substrates 36A and 36B are also electrically connected to each other by the flexible circuit substrates, which is not illustrated in the drawings.

As described above, the spacer 41 which is a substrate fixing portion for fixing the control substrate 37 to the housing 12 is made of metal and is a conductor. In contrast, the adhesive 39 which is a panel fixing portion for indirectly fixing each of the first and second sensor panels 11A and 11B to the housing 12 (fixing the base 28 to the housing 12) is made of a resin and is an insulator. Therefore, the adhesive 39 has a higher impedance than the spacer 41. In addition, a general LCR meter (impedance analyzer) can be used to measure the impedance. Examples of a specific measurement method include a two-terminal method, a four-terminal method, and a five-terminal method. The measurement method with a less error is the four-terminal method and the five-terminal method.

Figure 3:
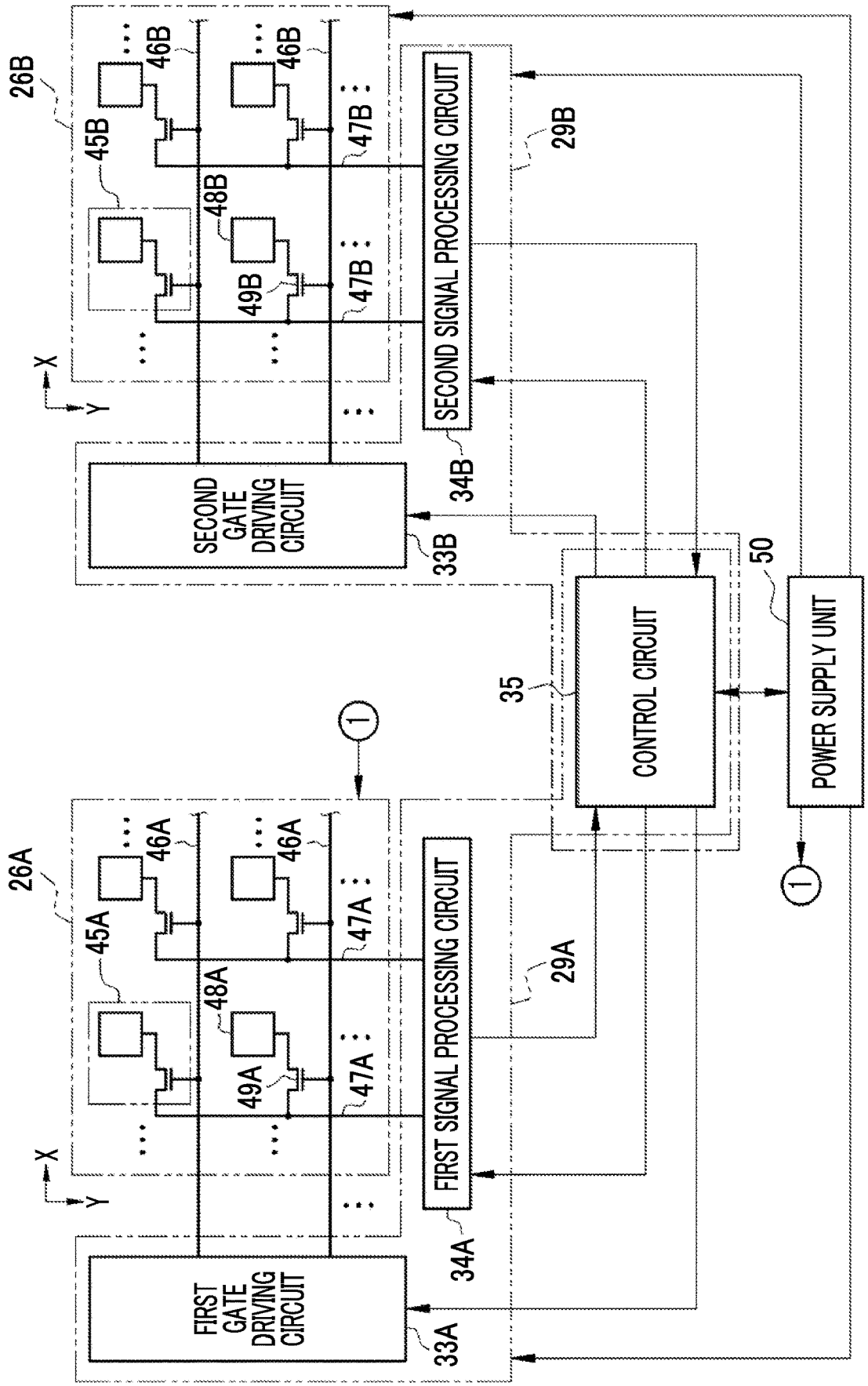
FIG. 3 is a block diagram illustrating the electrical configuration of the electronic cassette.

In FIG. 3, the first light detection substrate 26A is configured by providing first pixels 45A which are arranged in a two-dimensional matrix of N rows and M columns, N first gate lines 46A, and M first signal lines 47A on a glass substrate (not illustrated). The first gate lines 46A extend in the X direction along a row direction of the first pixels 45A and are arranged at a predetermined pitch in the Y direction along a column direction of the first pixels 45A. The first signal lines 47A extend in the Y direction and are arranged at a predetermined pitch in the X direction. The first gate lines 46A and the first signal lines 47A are orthogonal to each other and the first pixels 45A are provided so as to correspond to the intersection points between the first gate lines 46A and the first signal lines 47A.

N and M are integers that are equal to or greater than 2. For example, N is 2880 and M is 2304. In addition, the array of the first pixels 45A may be a square array as illustrated in FIG. 3. The first pixels 45A may be inclined at 45° and may be arranged in zigzag.

As is well known, the first pixel 45A comprises a first photoelectric conversion unit 48A on which visible light is incident and which generates charge (electron-hole pair) and accumulates the charge and a first thin film transistor (TFT) 49A. The first photoelectric conversion unit 48A has a structure in which an upper electrode and a lower electrode are provided on the upper and lower sides of a semiconductor layer that generates charge. The semiconductor layer is, for example, a p-intrinsic-n (PIN) type and includes an N-type layer provided on the upper electrode side and a P-type layer provided on the lower electrode side. The first TFT 49A has a gate electrode connected to the first gate line 46A, a source electrode connected to the first signal line 47A, and a drain electrode connected to the lower electrode of the first photoelectric conversion unit 48A. In addition, a light detection substrate that is not a TFT type, but is a complementary metal oxide semiconductor (CMOS) type may be used.

A bias line (not illustrated) is connected to the upper electrode of the first photoelectric conversion unit 48A. A positive bias voltage is applied to the upper electrode through the bias line. The positive bias voltage is applied to generate an electric field in the semiconductor layer. Therefore, in the electron-hole pair generated in the semiconductor layer by photoelectric conversion, the electron is moved to the upper electrode and is absorbed by the bias line and the hole is moved to the lower electrode and is collected as charge.

The second light detection substrate 26B has the same configuration as the first light detection substrate 26A. Therefore, alphabet "B" is added next to numbers for components of the second light detection substrate 26B to distinguish the components from the components of the first light detection substrate 26A and the description of the components will not be repeated.

The first gate driving circuit 33A is connected to the ends of the first gate lines 46A and generates a gate pulse for driving the first TFTs 49A. The control circuit 35 drives the first TFTs 49A through the first gate driving circuit 33A and controls the driving of the first signal processing circuit 34A to control the operation of the first sensor panel 11A. Specifically, the control circuit 35 directs the first sensor panel 11A to perform a pixel reset operation which reads dark charge from the first pixel 45A and resets (removes) the dark charge, a pixel charge accumulation operation which accumulates charge corresponding to the amount of X-rays reaching the first pixel 45A in the first pixel 45A, and an image reading operation which reads the charge accumulated in the first pixel 45A to the first signal processing circuit 34A through the first signal line 47A.

The first signal processing circuit 34A converts the accumulated charge read from the first pixel 45A by the image reading operation into an analog voltage signal. Then, the first signal processing circuit 34A performs a known correlated double sampling process for the analog voltage signal to remove a noise component from the analog voltage signal. Then, the first signal processing circuit 34A converts the analog voltage signal into a digital signal corresponding to the voltage value of the analog voltage signal (analog/digital conversion) and outputs the digital signal to the control circuit 35. The control circuit 35 stores the digital signal output from the first signal processing circuit 34A as an X-ray image (a first X-ray image, see FIG. 4) in an embedded memory (not illustrated). In addition, the second circuit unit 29B has the same configuration as the first circuit unit 29A. Therefore, as in the case of the second light detection substrate 26B, the description of the second circuit unit 29B is omitted.

The power supply unit 50 supplies power to the first and second sensor panels 11A and 11B and the first and second circuit units 29A and 29B under the control of the control circuit 35. The power supply unit 50 is provided with a switching power supply. The switching power supply converts a voltage based on power from a battery or a commercial power supply into a voltage suitable for the first and second sensor panels 11A and 11B and the first and second circuit units 29A and 29B using a pulse modulation method, for example, a pulse width modulation (PWM) method, and outputs the voltage.

Figure 4:
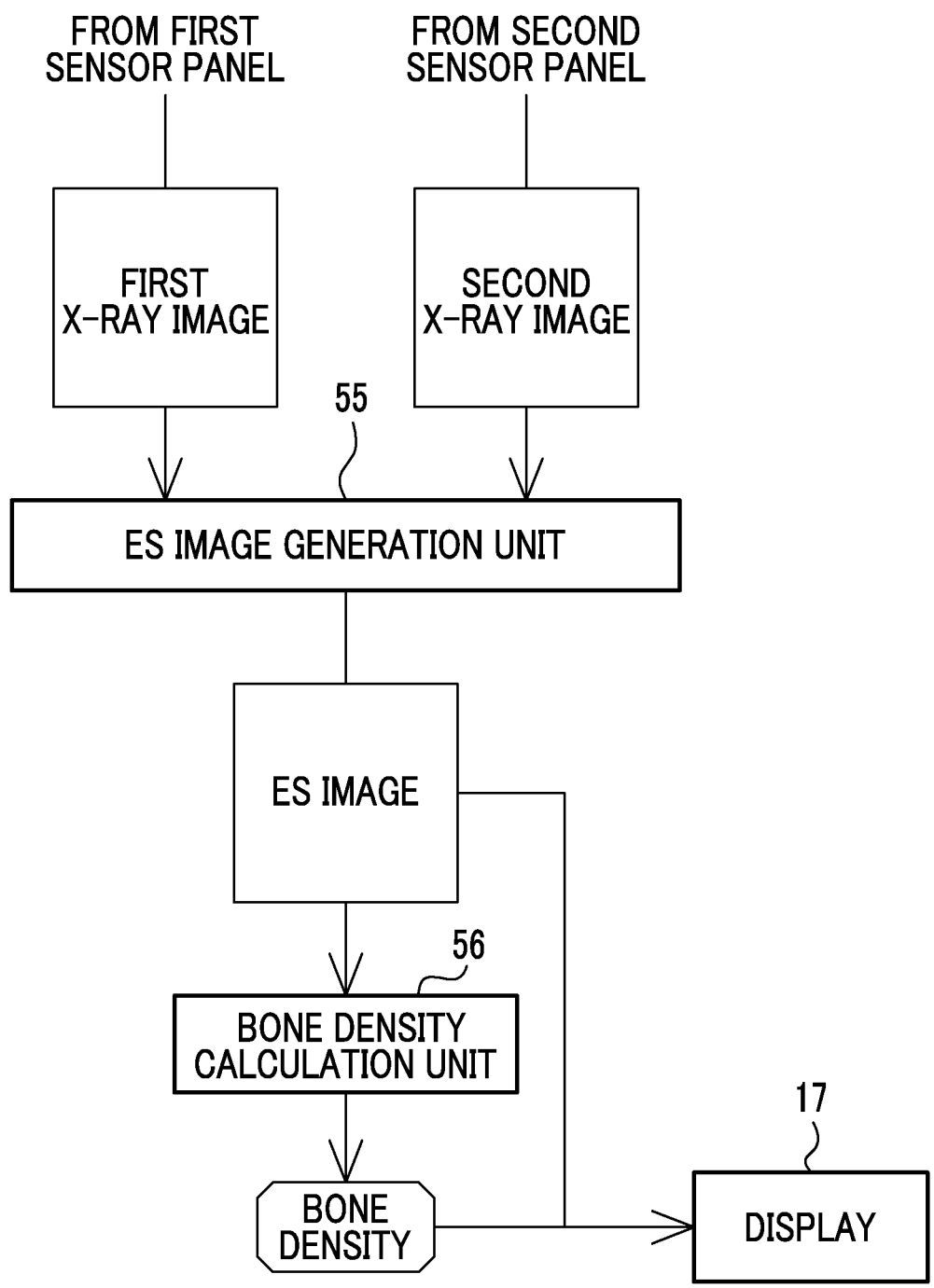
FIG. 4 is a block diagram illustrating the configuration of a console related to the calculation of bone density.

In FIG. 4, the console 16 receives a first X-ray image from the first sensor panel 11A and receives a second X-ray image from the second sensor panel 11B. The first X-ray image and the second X-ray image are based on the charge accumulated in the first and second pixels 45A and 45B in response to the X-rays which have been emitted from the X-ray source 15 and then transmitted through the subject H, respectively, and indicate the internal structure of the body of the subject H.

An offset correction process which removes artifacts caused by fixed pattern noise which is an example of noise caused by the usage environment of the electronic cassette 10, such as environmental temperature, is performed for the first X-ray image and the second X-ray image and then the first X-ray image and the second X-ray image are input to an ES image generation unit 55. The ES image generation unit 55 generates an ES image from the first X-ray image and the second X-ray image. Specifically, the ES image generation unit 55 subtracts an image obtained by multiplying the first X-ray image by a predetermined coefficient from an image obtained by multiplying the second X-ray image by a predetermined coefficient in units of pixels. The ES image generated by the subtraction process is, for example, an image in which soft tissues have been removed and bone tissues have been highlighted.

A bone density calculation unit 56 calculates bone density in an imaging part of the subject H as an index value related to bones. Specifically, first, the bone density calculation unit 56 analyzes the ES image from the ES image generation unit 55 to extract a bone tissue region of the ES image. Then, for example, the bone density calculation unit 56 multiplies a representative value (for example, the mean, maximum value, or mode) of the pixel values of the bone tissue region by a conversion coefficient for converting the pixel values into a bone mass to calculate the bone mass. The bone density calculation unit 56 divides the calculated bone mass by the area of the bone tissue region to calculate bone density.

The console 16 displays, for example, the bone density calculated by the bone density calculation unit 56 and the ES image generated by the ES image generation unit 55 on the display 17. As such, the X-ray images output from the first and second sensor panels 11A and 11B are used to calculate the index value related to bones. Further, in addition to or instead of the bone density, the bone mass may be displayed on the display 17.

For example, an application program related to X-ray imaging is executed to construct the ES image generation unit 55 and the bone density calculation unit 56 in a central processing unit (CPU) of the console 16. Some or all of the above-mentioned units may be constructed in the CPU of the electronic cassette 10 and the electronic cassette 10 may perform the generation of the ES image or bone density calculation.

Next, the operation of the above-mentioned configuration will be described. In a case in which X-ray imaging is performed for the subject H using the electronic cassette 10, the operator turns on the electronic cassette 10 and sets the electronic cassette 10 in the holder 14 of the imaging table 13. Then, the operator adjusts the positional relationship among the electronic cassette 10, the X-ray source 15, and the subject H and then operates the X-ray source 15 to emit X-rays.

The X-rays which have been emitted from the X-ray source 15 and then transmitted through the subject H are incident on the first sensor panel 11A and the second sensor panel 11B through the transmission plate 25. Each of the first and second sensor panels 11A and 11B receives the emitted X-rays and sequentially performs the pixel reset operation and the pixel charge accumulation operation. The charge corresponding to the amount of X-rays reaching each of the first and second pixels 45A and 45B is accumulated in each of the first and second pixels 45A and 45B.

After the emission of the X-rays ends, the image reading operation is performed in each of the first and second sensor panels 11A and 11B. Then, the first X-ray image and the second X-ray image are output from the first sensor panel 11A and the second sensor panel 11B, respectively.

It has been known that electromagnetic noise is generated from a circuit substrate by the operation of various circuits. In this embodiment, the electromagnetic noise is mainly high-frequency noise that is generated from the control substrate 37 of the control circuit 35 having a relatively high operating frequency.

Figure 5:
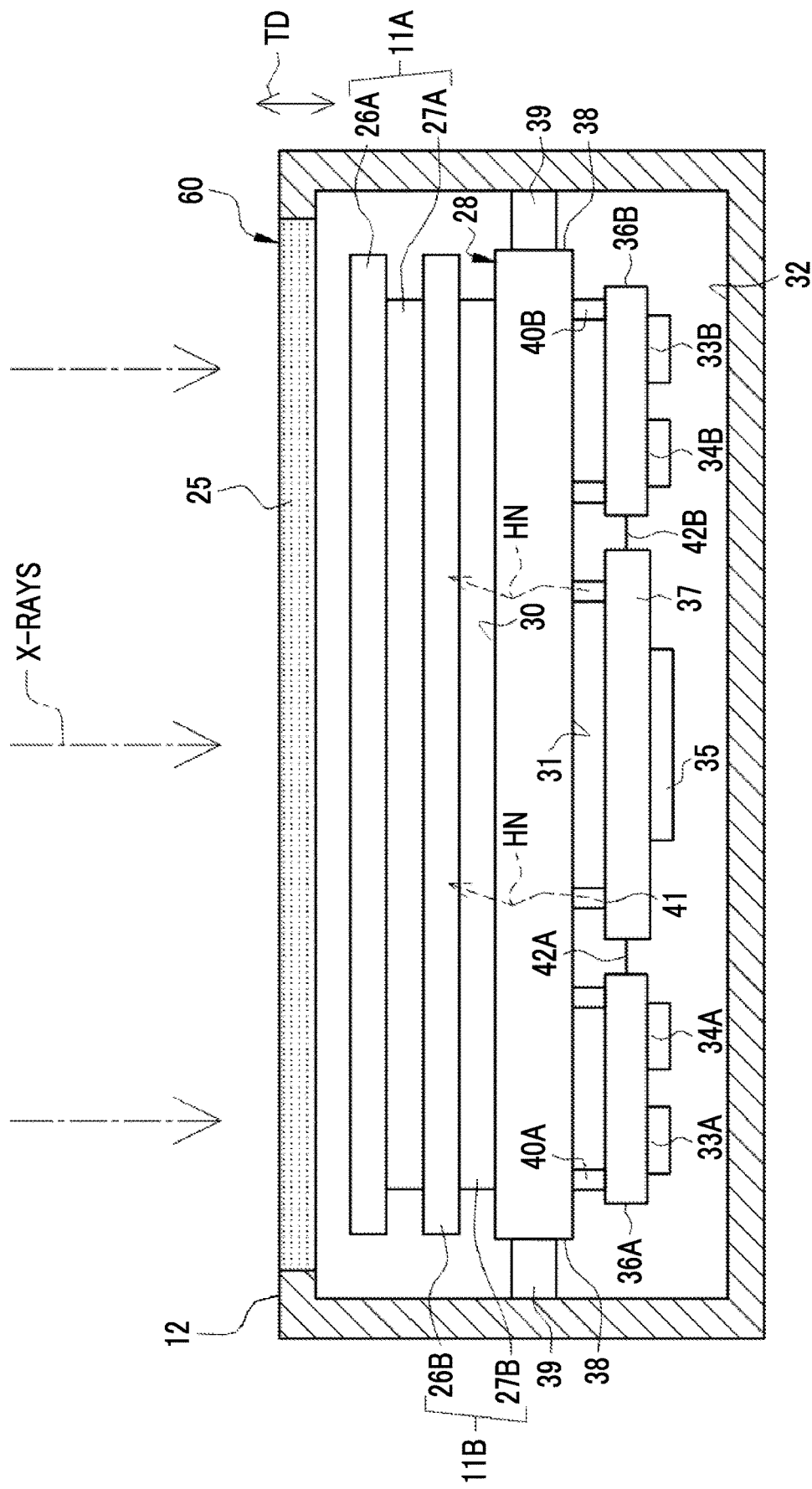
FIG. 5 is a diagram illustrating the internal structure of an electronic cassette according to the related art.

FIG. 5 illustrates an electronic cassette 60 according to the related art in which all of circuit substrates 36A, 36B, and 37 are mounted and fixed to a rear surface 31 of a base 28 as in JP2013-250103A. In this case, the control substrate 37 is mounted and fixed to the rear surface 31 of the base 28 through spacers 41 made of metal. Each of sensor panels 11A and 11B is attached to a front surface 30 of the base 28. Therefore, a path through (represented by a dashed arrow HN) which the high-frequency noise generated by the control substrate 37 is propagated to each of the sensor panels 11A and 11B is relatively short and is linear. Therefore, the impedance of the propagation path of the high-frequency noise is relatively low. As a result, the high-frequency noise generated by the control substrate 37 is propagated to each of the sensor panels 11A and 11B through the spacers 41 and the base 28 and it is highly likely that the quality of each X-ray image is degraded.

However, in the invention, as illustrated in FIG. 2, the control substrate 37 is fastened and fixed to the inner surface 32 of the housing 12 by the spacers 41. The control substrate 37 is fixed only to the housing 12 through the spacers 41. Therefore, the path through which the high-frequency noise generated by the control substrate 37 is propagated to each of the first and second sensor panels 11A and 11B is longer than that illustrated in FIG. 5 and is not linear. In this case, the impedance of the propagation path of the high-frequency noise is higher than that illustrated in FIG. 5.

The high-frequency noise generated by the control substrate 37 is mainly propagated to the housing 12. However, since the impedance of the propagation path of the high-frequency noise is relatively high in the electronic cassette 10 as described above, the high-frequency noise is less likely to be propagated to each of the first and second sensor panels 11A and 11B than that in JP2013-250103A. The housing 12 is a box with a rectangular parallelepiped shape and has a larger size than the base 28 with a thin plate shape. Therefore, even in a case in which the high-frequency noise is propagated to the housing 12, the high-frequency noise is likely to be attenuated and removed before it is propagated to each of the first and second sensor panels 11A and 11B. Thus, in the invention, the possibility that electromagnetic noise generated by a circuit substrate, particularly, high-frequency noise generated by the control substrate 37 will be propagated to each of the first and second sensor panels 11A and 11B and the quality of each X-ray image will be degraded can be lower than that in the structure disclosed in JP2013-250103A.

In addition, as illustrated in FIG. 2, the base 28 is fixed to the inner surface 32 of the housing 12 through the adhesive 39 having a higher impedance than the spacer 41. Therefore, it is possible to further increase the impedance of the propagation path of the high-frequency noise that is generated by the control substrate 37 and is propagated to the housing 12. Thus, the high-frequency noise is blocked by the adhesive 39 and is hardly propagated to the base 28. In addition, each of the first and second sensor panels 11A and 11B is indirectly fixed to the housing 12 through the base 28 and is not directly fixed to the housing 12. Therefore, the probability that the high-frequency noise generated by the control substrate 37 will be finally propagated to each of the first and second sensor panels 11A and 11B can be very low. In FIG. 5, the first and second circuit units 29A and 29B are not illustrated.

Each X-ray image is transmitted from the electronic cassette 10 to the console 16. In the console 16, as illustrated in FIG. 4, the ES image generation unit 55 generates an ES image and the bone density calculation unit 56 calculates bone density on the basis of the ES image. The bone density is displayed on the display 17 together with, for example, the ES image.

In a case in which the quality of the X-ray image which is the origin of the calculation of the index value related to bones, such as bone density, is not guaranteed, there is a concern that the reliability of the index value will be significantly reduced. However, in the invention, since the quality of the X-ray image is guaranteed at a relatively high level, it is possible to improve the reliability of the index value.

In the configuration in which the first and second sensor panels 11A and 11B are sequentially arranged in the thickness direction, the amount of radiation reaching the second sensor panel 11B is reduced to 10% to 20% of the amount of radiation reaching the first sensor panel 11A. Therefore, the signal-noise (SN) ratio of the second X-ray image is reduced. In a case in which electromagnetic noise is propagated, the influence of the electromagnetic noise is relatively large. Therefore, the invention is effective in the configuration in which the first and second sensor panels 11A and 11B are sequentially arranged in the thickness direction.

Second Embodiment

Figure 6:
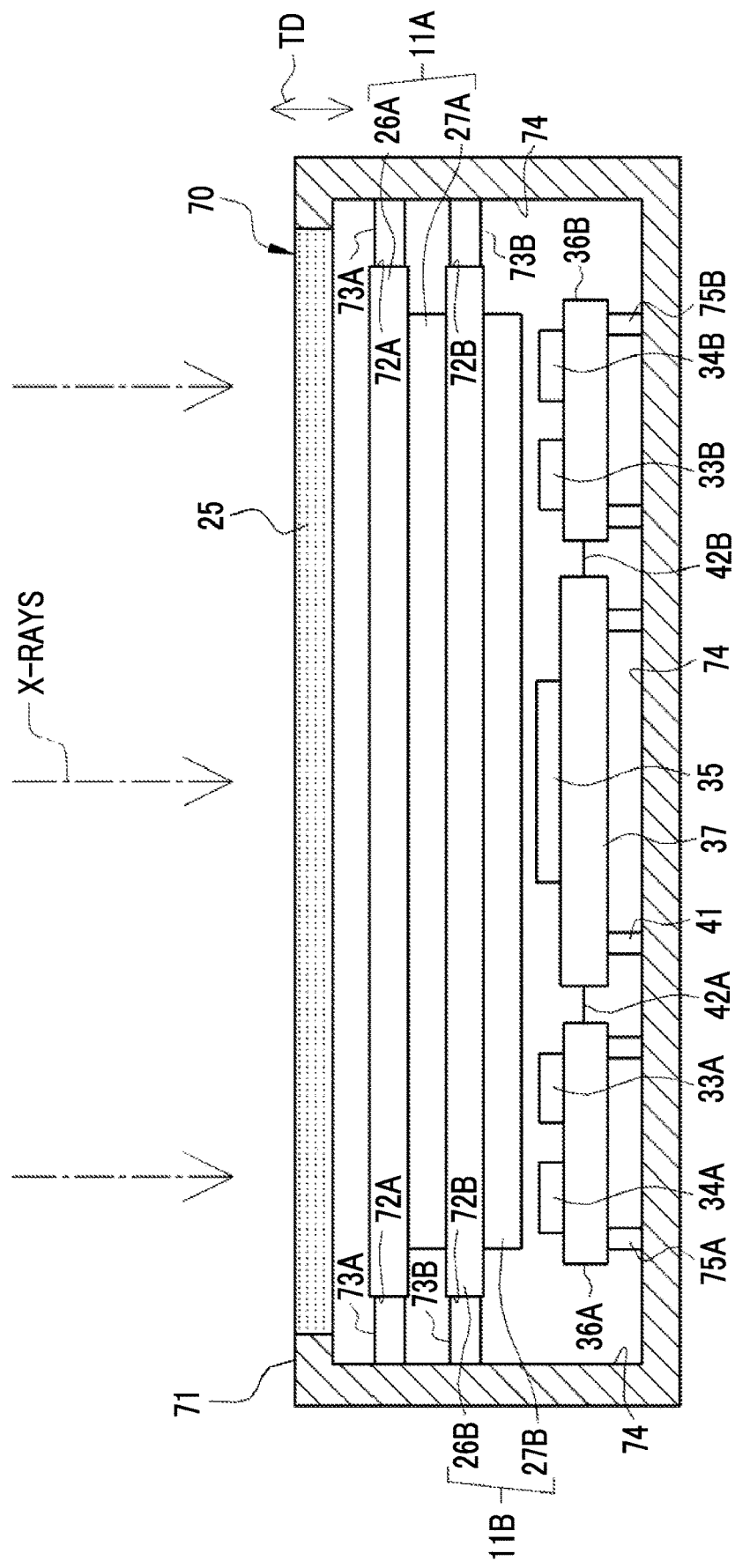
FIG. 6 is a diagram illustrating the internal structure of an electronic cassette according to a second embodiment.

An electronic cassette 70 according to a second embodiment illustrated in FIG. 6 is the same as the electronic cassette 10 according to the first embodiment illustrated in FIG. 2 in the configuration of, for example, the first and second sensor panels 11A and 11B and differs from the electronic cassette 10 in that the base 28 is not provided. Therefore, the first and second sensor panels 11A and 11B are directly fixed to a housing 71 instead of being fixed to the housing through the base 28.

Specifically, a portion or all of a first side surface 72A which is an outer surface of the first light detection substrate 26A in the first sensor panel 11A is fixed to an inner surface (an inner side surface of the housing 71) 74 of the housing 71 by a first adhesive 73A. Similarly, a portion or all of a second side surface 72B which is an outer surface of the second light detection substrate 26B in the second sensor panel 11B is fixed to the inner surface (the inner side surface of the housing 71) 74 of the housing 71 by a second adhesive 73B. Each of the first and second adhesives 73A and 73B is made of a resin, such as an epoxy resin, similarly to the adhesive 39 according to the first embodiment and corresponds to a panel fixing portion that directly fixes each of the first and second sensor panels 11A and 11B to the housing 71.

In the electronic cassette 70, in addition to the control substrate 37, the first and second circuit substrates 36A and 36B are mounted and fixed to the inner surface (an inner rear surface of the housing 71) 74 of the housing 71 through a first spacer 75A and a second spacer 75B which are made of metal such as aluminum, copper, or stainless steel, respectively. The first and second spacers 75A and 75B are vertically provided on the inner surface (the inner rear surface of the housing 71) 74 of the housing 71 and are fastened and fixed to the first and second circuit substrates 36A and 36B, respectively. In the second embodiment, each of the first and second spacers 75A and 75B also corresponds to the substrate fixing portion and each of the first and second circuit substrates 36A and 36B also corresponds to the specific substrate.

In this case, similarly to the first embodiment, the first and second adhesives 73A and 73B which are the panel fixing portions have a higher impedance than the spacers 41, 75A, and 75B which are the substrate fixing portions. In addition to the control substrate 37, the first and second circuit substrates 36A and 36B are mounted and fixed to the inner surface 74 of the housing 71. Therefore, electromagnetic noise is less likely to be propagated to each of the first and second sensor panels 11A and 11B. Thus, in the configuration of the electronic cassette 70, it is possible to effectively suppress the propagation of the electromagnetic noise generated by the first and second circuit substrates 36A and 36B and the control substrate 37, particularly, the high-frequency noise generated by the control substrate 37 to each of the first and second sensor panels 11A and 11B. It is possible to further reduce the possibility that the quality of each X-ray image will be degraded. In FIG. 6, the first and second circuit units 29A and 29B are not illustrated similarly to FIG. 5.

In the electronic cassette 10 having the base 28 according to the first embodiment, the first and second circuit substrates 36A and 36B may be mounted and fixed to the inner surface 32 of the housing 12 as in the second embodiment.

The substrate fixing portion is not limited to the metal spacer illustrated in each of the above-described embodiments. For example, the substrate fixing portion may be a conductive adhesive for attaching the circuit substrate to the inner surface of the housing. Similarly, the panel fixing portion is not limited thereto the resin adhesive illustrated in each of the above-described embodiments. For example, the panel fixing portion may include a resin bridge plate for connecting the outer surface of the sensor panel and the inner surface of the housing and a resin attachment screw for fastening and fixing the bridging plate to the outer surface of the sensor panel and the inner surface of the housing.

The state in which "two sensor panels are sequentially arranged in the thickness direction" is not limited to the state in which two sensor panels are closely arranged as in each of the above-described embodiments. The state in which "two sensor panels are sequentially arranged in the thickness direction" also includes a state in which two sensor panels are not closely arranged and are separated from each other with a gap therebetween and a state in which an insert, such as an X-ray filter for restricting the incidence of soft ray components of X-rays, is interposed between two sensor panels.

In each of the above-described embodiments, the electronic cassette in which two sensor panels 11A and 11B are sequentially arranged in the thickness direction TD is given as an example. However, the invention is not limited thereto. The invention can also be applied to an electronic cassette including one sensor panel.

In each of the above-described embodiments, the electronic cassette is given as an example of the radiographic image detection device. However, the invention is not limited thereto. The invention can also be applied to a stationary radiographic image detection device that is fixed to the imaging table. In addition, the invention is not limited to X-rays and can also be applied to a case in which other types of radiation, such as γ-rays, are used.

The conjunction "or" described in the specification is not an expression intended to be a limited interpretation of any one of a plurality of options connected by the conjunction depending on the context, but is an expression including combinations of the plurality of options. For example, a sentence "an option A or an option B is performed" needs to be interpreted as having the following three meanings, depending on the context: "an option A is performed"; "an option B is performed"; and "an option A and an option B are performed".

The invention is not limited to each of the above-described embodiments and various configurations may be used as long as they do not depart from the scope and spirit of the invention.

EXPLANATION OF REFERENCES 10, 60, 70: electronic cassette (radiographic image detection device)
11A: first sensor panel
11B: second sensor panel
12, 71: housing
13: imaging table
14: holder
15: X-ray source (radiation source)
16: console
17: display
18: input device
25: transmission plate
26A, 26B: first and second light detection substrates
27A, 27B: first and second scintillators
28: base
29A, 29B: first and second circuit unit
30: front surface of base
31: rear surface of base
32, 74: inner surface of housing
33A, 33B: first and second gate driving circuits
34A, 34B: first and second signal processing circuits
35: control circuit
36A, 36B: first and second circuit substrates (circuit substrates other than specific circuit, specific substrates)
37: control substrate (specific substrate)
38: side surface of base (outer surface of base)
39: adhesive (panel fixing portion)
40A, 40B: first and second spacers
41: spacer (substrate fixing portion)
42A, 42B: first and second flexible circuit substrates
45A, 45B: first and second pixels
46A, 46B: first and second gate lines
47A, 47B: first and second signal lines
48A, 48B: first and second photoelectric conversion units
49A, 49B: first and second TFTs
50: power supply unit
55: ES image generation unit
56: bone density calculation unit
72A, 72B: first and second side surfaces (outer surfaces of each sensor panel) of first and second light detection substrates
73A, 73B: first and second adhesive (panel fixing portion)
75A, 75B: first and second spacer (substrate fixing portion)
H: subject
TD: thickness direction
X: row direction of pixel
Y: column direction of pixel
HN: high-frequency noise

What is claimed is:

1. A radiographic image detection device comprising:
a sensor panel in which pixels that accumulate charge in response to radiation, which has been emitted from a radiation source and transmitted through a subject, are two-dimensionally arranged;
a circuit unit that converts the charge into a digital signal, outputs the digital signal as a radiographic image, and includes circuit substrates on which various circuits are mounted;
a conductive housing that accommodates the sensor panel and the circuit unit; and
a conductive substrate fixing portion that fixes a specific substrate which is at least one of the circuit substrates to the housing,
wherein the specific substrate is directly fixed to an inner surface of a rear surface of the housing through the substrate fixing portion, the rear surface being opposite to a front surface of the housing on which the radiation is incident.

2. The radiographic image detection device according to claim 1, further comprising:
a panel fixing portion that fixes the sensor panel to the housing,
wherein the panel fixing portion has a higher impedance than the substrate fixing portion.

3. The radiographic image detection device according to claim 2,
wherein the panel fixing portion directly fixes the sensor panel to the housing.

4. The radiographic image detection device according to claim 3,
wherein the substrate fixing portion is a spacer that is made of metal, is vertically provided on an inner surface of the housing, and is fastened and fixed to the specific substrate, and
the panel fixing portion is an adhesive that is made of a resin and bonds an outer surface of the sensor panel and the inner surface of the housing.

5. The radiographic image detection device according to claim 1,
wherein the specific substrate fixed to the housing through the substrate fixing portion includes a control substrate having a control circuit that controls an operation of the sensor panel.

6. The radiographic image detection device according to claim 1,
wherein two sensor panels are provided and are sequentially arranged in a thickness direction, and two circuit units are provided for the two sensor panels, respectively.

7. The radiographic image detection device according to claim 6, wherein two radiographic images output from the two circuit units are used to calculate an index value related to bones.

8. A radiographic image detection device comprising:

a sensor panel in which pixels that accumulate charge in response to radiation, which has been emitted from a radiation source and transmitted through a subject, are two-dimensionally arranged;

a circuit unit that converts the charge into a digital signal, outputs the digital signal as a radiographic image, and includes circuit substrates on which various circuits are mounted;

a conductive housing that accommodates the sensor panel and the circuit unit;

a conductive substrate fixing portion that fixes a specific substrate which is at least one of the circuit substrates to the housing;

a panel fixing portion that fixes the sensor panel to the housing; and a base having a front surface to which the sensor panel is attached, wherein the specific substrate is fixed to the housing through the substrate fixing portion, wherein the panel fixing portion has a higher impedance than the substrate fixing portion, wherein the panel fixing portion fixes the base to the housing, and the sensor panel is indirectly fixed to the housing through the base.

9. The radiographic image detection device according to claim 8, wherein the substrate fixing portion is a spacer that is made of metal, is vertically provided on an inner surface of the housing, and is fastened and fixed to the specific substrate, and the panel fixing portion is an adhesive that is made of a resin and bonds an outer surface of the base and the inner surface of the housing.

10. The radiographic image detection device according to claim 8, wherein the circuit substrates other than the specific substrate are mounted and fixed to a rear surface of the base.

\* \* \* \* \*